(12) United States Patent
Neuberger

(10) Patent No.: US 6,562,295 B1
(45) Date of Patent: May 13, 2003

(54) BACTERIA RESISTANT MEDICAL DEVICES

(75) Inventor: Wolfgang Neuberger, F.T. Labuan (MY)

(73) Assignee: CeramOptec Industries, Inc., East Longmeadow, MA (US)

( * ) Notice: Subject to any disclaimer, the term of this patent is extended or adjusted under 35 U.S.C. 154(b) by 0 days.

(21) Appl. No.: 09/345,282

(22) Filed: Jun. 30, 1999

(51) Int. Cl.[7] .................................................. A16L 2/00
(52) U.S. Cl. ............................ 422/22; 422/24; 422/28; 422/29; 514/2; 514/185
(58) Field of Search ............................ 422/22, 24, 28, 422/29; 514/2, 185; 604/265

(56) References Cited

U.S. PATENT DOCUMENTS

| | | | |
|---|---|---|---|
| 4,054,719 A | * 10/1977 | Cordes, III | 428/461 |
| 4,295,948 A | * 10/1981 | Roman et al. | 428/463 |
| 4,476,590 A | 10/1984 | Scales et al. | 3/1.91 |
| 4,786,658 A | * 11/1988 | Hashimoto et al. | 522/121 |
| 5,217,493 A | * 6/1993 | Raad et al. | 623/11 |
| 5,260,020 A | 11/1993 | Wilk et al. | 422/22 |
| 5,399,583 A | * 3/1995 | Levy et al. | 514/410 |
| 5,470,307 A | * 11/1995 | Lindall | 604/20 |
| 5,516,629 A | * 5/1996 | Park et al. | 435/2 |
| 5,611,793 A | 3/1997 | Wilson et al. | 606/2 |
| 5,679,661 A | * 10/1997 | Willey | 514/63 |

* cited by examiner

*Primary Examiner*—Krisanne Thornton
(74) *Attorney, Agent, or Firm*—Bolesh J. Skutnik; BJ Associates

(57) ABSTRACT

A novel approach to fight bacterial growth on and attachment to medical devices/implants is described. This approach reduces the necessity of the painful and complicated replacement of the medical devices that frequently need to remain in the body for periods of time longer than is recommended using a traditionally sterilized device. Several methods are described to kill bacteria that have attached to the surface of medical devices. Long term use is then possible with those medical devices. Furthermore a medical device is described under this method that has a photosensitizing compound affixed to or near the device surface with means to periodically activate the compound by suitable illumination.

22 Claims, 2 Drawing Sheets

BACTERIA RESISTANT MEDICAL DEVICES

BACKGROUND OF THE INVENTION

1. Field of the Invention

The present invention relates to devices, such as catheters, that can be used inside the body for extended periods of time. Several methods are described to facilitate the destruction of bacteria without the necessity of removal of a medical device.

2. Invention Disclosure Statement

Bacteria are present on the surface of the skin and throughout the bodies of humans and animals. Not all of the bacteria are harmful, but medical instruments must be sterilized to prevent harmful bacteria from infecting wounds or incisions. Sterilization before use is sufficient for short-term use instruments, those that remain in contact with the body for less than forty-eight hours, because those medical instruments are generally removed before significant bacterial growth can occur.

Medical devices that remain in the body of humans or animals for longer periods of time create an ideal attachment surface and growth area for bacteria. Furthermore, introduction of medical devices into the body allows bacteria to bypass the subcutaneous layers. The resulting infections can be harmful or even deadly. Current art devices such as catheters can only remain inside the body for a limited amount of time before they must be removed and replaced with a sterilized device. The removal and replacement of these longer-term devices can be complicated and raise the cost of medical care. Removal and replacement is often painful for the patient. Various methods have been proposed to prevent the attachment of bacteria to medical devices as well as destroy bacteria once the device is in the body. One approach has been to incorporate. antibiotics into the medical device materials or onto their surfaces. This method is insufficient because a limited amount of antibiotics can be applied to these surfaces. This limited amount of antibiotic is quickly depleted and used up. Many of the medical devices used in vivo need to remain inside the body for periods of time that are longer than antibiotics can last.

Another approach has been to manufacture the medical device out of a bacteria resistant substance. Along the same line, U.S. Pat. No. 4,476,590 describes an endoprosthetic implant that utilizes an activated silver coating to resist bacteria. One problem that exists with this method is that once the silver coating is activated the effect can not be otherwise controlled. Yet another problem recognized by the above patent is that the silver coating itself may cause damage to connective tissue. The use of a silver coating on medical devices has proved to be mostly unsuccessful in controlling bacterial growth while adding to the cost of manufacturing the medical device.

In a related area of the PDT prior art, U.S. Pat. No. 5,611,793 describes a topical method to disinfect or sterilize tissue in the oral cavity. This method is concerned with disinfecting an accessible area in the mouth and deals strictly with open areas such as wounds or lesions particular to the oral cavity. A photosensitizer, in a solution or gel form, must be applied directly to the sites to be sterilized. The sites are subsequently exposed with a suitable laser light. This method contemplates the use of photosensitizer treatment to sterilize the mouth before surgery, to treat a diagnosed infection, or as a preventative measure for diseases which affect the oral cavity. This is a one-time treatment and the photosensitizer gel or solution must be reapplied whenever sterilization treatment is necessary.

U.S. Pat. No. 5,260,020 describes a catheter that utilizes ultraviolet or infared radiation or other heat producing sources to sterilize the catheter while it remains in vivo. These methods are very non-specific as to its target and could result in the destruction of host cells as well as the targeted bacteria. The ultraviolet radiation proposed is known to kill most living cells, bacteria and host tissue alike. Ultraviolet radiation also has the added problem of an increase in a risk of cancer. Another proposal of '020, is the use of infared radiation to sterilize the catheter. The problem with using infared radiation or the other thermal methods proposed is, that at the intensity level required, damage to surrounding tissue is likely to occur from this prolonged thermal exposure. Conversely, the present invention utilizes a lightsource with a lower intensity and safer wavelength.

It is therefore the goal of the present invention to provide a method to shield/defend medical device surfaces against bacterial growth. The current invention will protect the surfaces of the device for the weeks or months that are frequently required. The problem of bacterial growth on and adherence to medical devices can be overcome by the utilizing the current invention method.

BRIEF SUMMARY OF THE INVENTION

It is an object of the present invention to provide a medical device that will have a reduced possibility of bacterial adherence on its surfaces.

It is also an object of the present invention to provide medical devices that can be kept free of bacteria for extended periods of time during in vivo use.

Another object of the present invention is to provide a method to deter bacterial growth on medical device surfaces by periodically activating a coating, which is capable of inhibiting bacterial growth on the medical device.

It is a further object of the present invention to describe methods to activate a photosensitized coating on a medical device so that the need to remove the device can be avoided.

Briefly stated, the present invention provides a novel approach to fight bacterial growth on and attachment to medical devices. This approach reduces the necessity of the painful and complicated replacement of medical devices that frequently need to remain in the body for periods of time longer than is recommended using a traditionally sterilized device. Several methods are described to kill bacteria that have attached to the surface of medical devices. Long term use is then possible with those medical devices. Furthermore a medical device is described under this method that has a photosensitizing compound affixed to or near the device surface with means to periodically activate the compound by suitable illumination. Several methods are described by which to provide illumination to the photosensitizer near a bacteria growth and attachment site.

The above and other objects, features and advantages of the present invention will become apparent from the following description read in conjunction with the accompanying drawings.

DETAILED DESCRIPTION OF PREFERRED EMBODIMENTS

Figure 1:
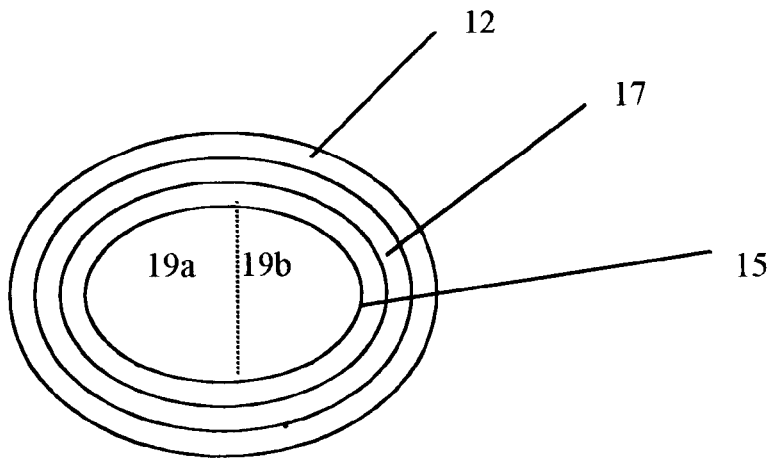
FIG. 1 shows a cross-sectional view of the distal end of a catheter according to the present invention.

Photosensitizers have been effectively used in fighting cancer and undesired cell proliferation, as well as in the destruction of bacteria. Once the chosen photosensitizer is irradiated by light of a suitable wavelength it acts as a catalyst for the generation of singlet oxygen. Singlet oxygen is a very reactive molecule that rapidly oxidizes the cellular components surrounding it. The use of singlet oxygen is effective in the destruction of bacteria as well as effective for its prior use in cancer treatments.

Since medical device surfaces are susceptible to bacterial growth and adherence while in vivo, it is advantageous if photosensitizers are utilized on those surfaces. Catheters and medical taps are particularly prone to infection. Semi permanent implants such as artificial teeth are also prone to bacterial infection because they create ideal pockets for bacteria to grow in. Catheters for example must be removed and replaced periodically to prevent bacteria from harming the patient. If the bacterial growth on and adherence to the catheter could be minimized, the catheter could remain inside the body for much longer periods of time with a reduced risk of infection and complications.

A medical device surface is manufactured with a photosensitizer coating. A specifically chosen photosensitizing compound, on the surface of the device, is a catalyst for singlet oxygen. Instead of using light energy to directly kill the bacteria, the appropriate wavelength of light activates the coating. The singlet oxygen rapidly oxidizes the cellular components surrounding it and therefore kills the bacteria. The present invention targets the bacteria and keeps it from adhering to and growing on the device surface while minimizing the risk of damage to surrounding tissue.

Several preferred method embodiments are possible. In the first, a suitable photosensitizer is immobilized on a device's surface and the area prone to microbial attack is periodically irradiated. Alternatively, a suitable photosensitizer is released in a controlled manner from the device's surface or from/through its surface layer. The photosensitizer is then in close proximity to or in contact with the bacteria when the area is subsequently irradiated. Finally, a suitable photosensitizing compound can be introduced from an outside source. The medical device is designed so that either the photosensitizing compound can be introduced directly to the medical device surface, or that the introduced photosensitizing compound will permeate or leach through to the medical device's surface.

Some medical devices are intended to remain in contact with the body for a long and undetermined amount of time. For example an artificial tooth implant is screwed into a patient's palate and potentially left in the mouth for years. One problem is that the oral cavity has more bacteria present than skin surfaces. The artificial tooth creates difficult to reach pockets that could promote bacterial growth. One embodiment of the present invention is an artificial tooth implant manufactured with optical light guides inside the tooth. These light guides direct applied light from an outer accessible surface of the tooth to the bacterial growth area. Since a photosensitizing coating would not necessarily last long enough in the oral cavity, the artificial tooth alternatively also incorporates means for applying the photosensitizer. A modified artificial tooth includes pores or channels that allow the photosensitizer to pass from a surface portion of the tooth to the bacterial growth areas. The photosensitizer is subsequently photo-activated to destroy the bacteria in the pocket of bacterial growth.

In another embodiment of the present invention, it is possible to initiate the periodic release of the photosensitizer from or through the device's surface by suitable means such as light exposure with a suitable first wavelength. This initial exposure brings the photosensitizer from some dormant state, to a state that can be activated. Alternatively this initial exposure triggers the release of the photosensitizer. This initial exposure and release of photosensitizer would be followed by exposure of the site with a second wavelength, which is appropriate to activate the photosensitizer and generate to singlet oxygen. This second exposure would take place after a suitable time interval has elapsed from the first irradiation, either to allow the optimum take up of the photosensitizer by the target bacteria or the optimum contact and proximity by the photosensitizer to the target bacteria.

Generally, embodiments of the current invention will make use of either a photosensitizer in the form of a coating on a medical device, or a photosensitizer that can be released from or through the surface and then remain in the vicinity of surface of the medical device.

EXAMPLE 1

A preferred embodiment of the current invention is depicted in FIG. 1. A catheter is inserted through the urinary tract to enable urine drainage. Catheter 17 is manufactured with the photosensitive substance immobilized on its cylindrical outer surface 12. The coating is immobilized on any distal surface that will remain in contact with the body. Surface 12 is in contact with the body when catheter 17 is inserted into the body. Inner surface 15 of lumen 19 can also be coated when advantageous. In situations where there is some likelihood of back flow through lumen 19, a coating on inner surface 15 will reduce bacterial contamination into the body from lumen area 19. A suitable fiber can then be inserted and withdrawn through one or more lumen 19a and 19b. The proximal end of the fiber is connected to a medical laser of suitable wavelength and output set at some predetermined rate. The fiber is then withdrawn at some predetermined rate to irradiate an extended section of the catheter. The dosage that is consequently applied per square unit surface area on the catheter's inner and outer surface is chosen to be sufficient to kill bacteria that have grown on and attached to those surfaces. The material used to manufacture the catheter is essentially transparent or sufficiently translucent to the wavelength required for photosensitizer activation. Before insertion into the body, the catheter is contained in an envelope that is either light tight to prevent premature bleaching of the photosensitizer from its exposure to daylight or artificial light or the envelope can be impenetrable to those wavelengths resulting in bleaching of the photosensitizer.

EXAMPLE 2

Figure 2:
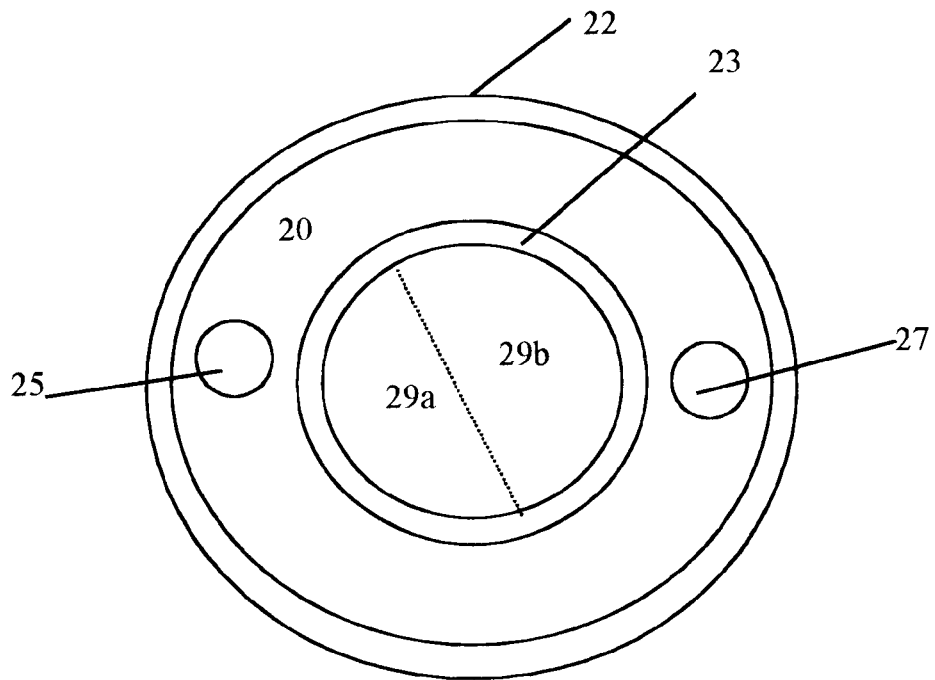
FIG. 2 shows the present invention cross-sectional view of distal end of a catheter with additional port(s) for a fiber.

In another embodiment of the present invention, a catheter, as depicted in FIG. 2, is described that allows fibers to be inserted and pushed up to the distal end through single or multiple ports on the catheters' proximal end. The use of these ports allows the catheter lumen to be used strictly for medical purposes without any interruption by an optical fiber. Catheter 20 is manufactured with the photosensitive substance immobilized on its cylindrical outer surface 22. The coating is immobilized on any distal surface that will remain in contact with the body. Outer surface 22 is in contact with the body when catheter 20 is inserted into the body. Inner surface 23 of lumen 29 can also be coated when advantageous. For example, in situations where there is some likelihood of back flow through lumen 29, a coating on inner surface 23 will reduce bacterial contamination into the body from lumen area 29. Single or multiple lumen 29 allow for drainage from the body, however one or more separate ports 25 and 27 in the catheter wall 20 allow for the insertion of a suitable fiber.

A suitable fiber can then be inserted and withdrawn through one or more ports 25 and 27. The proximal end of the fiber is connected to a medical laser of suitable wavelength and output set at some predetermined rate. The fiber is then withdrawn at some predetermined rate to irradiate an extended section of the catheter. The dosage that is consequently applied per square unit surface area on the catheter's inner and outer surface is chosen to be sufficient to kill bacteria that have grown on and attached to those surfaces. Alternatively, the fiber has a scattering coating over its entire length. The material used to manufacture the catheter is essentially transparent or sufficiently translucent to the wavelength required for photosensitizer activation. Before insertion into the body, the catheter is contained in an envelope that is either light tight to prevent premature bleaching of the photosensitizer from its exposure to daylight or artificial light or the envelope can be impenetrable to those wavelengths resulting in bleaching of the photosensitizer.

EXAMPLE 3

Figure 3:
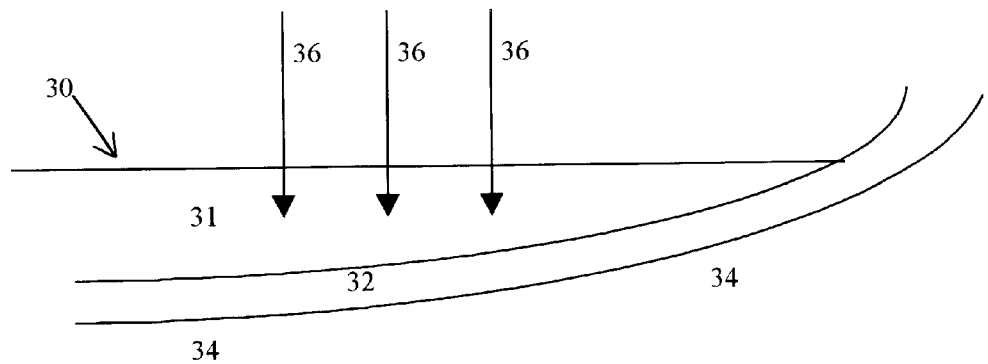
FIG. 3 depicts the irradiation of the present invention medical device through the surface of the skin.

In another preferred embodiment of the present invention, an implanted device (such as a catheter needle) is sitting close below the body's outer surface as depicted in FIG. 3. In this instance, radiation 36 of a suitable wavelength and intensity passes through skin 30 and tissue 31 from an external source (not shown). This method avoids using an internal space altogether, while other embodiments of the present invention need some existing lumen or port to deliver radiation. The device itself does not need to be disturbed or moved in order to illuminate it. An advantage to this method is that the medical device can be made to a minimal size, since no additional space is needed for an optical fiber. Another reason this method could be preferable is that either there isn't an existing lumen or that it is critical to have an uninterrupted flow through the lumen. Inserting a fiber through an existing lumen could interrupt or stop the flow of medication being delivered through that lumen. The proximal end of the lumen may be inaccessible or the lumen walls may be thin and easily damaged. This method also avoids the risk of external contamination from the optical fiber itself into the body. In this method, external radiation 36 activates photosensitizing coating 32 of medical device 34. Since photosensitizing coating 32 is on the surface of the device, singlet oxygen is generated at or near medical device 34 to destroy existing bacteria without any significant effect on surrounding tissue.

EXAMPLE 4

Figure 4:
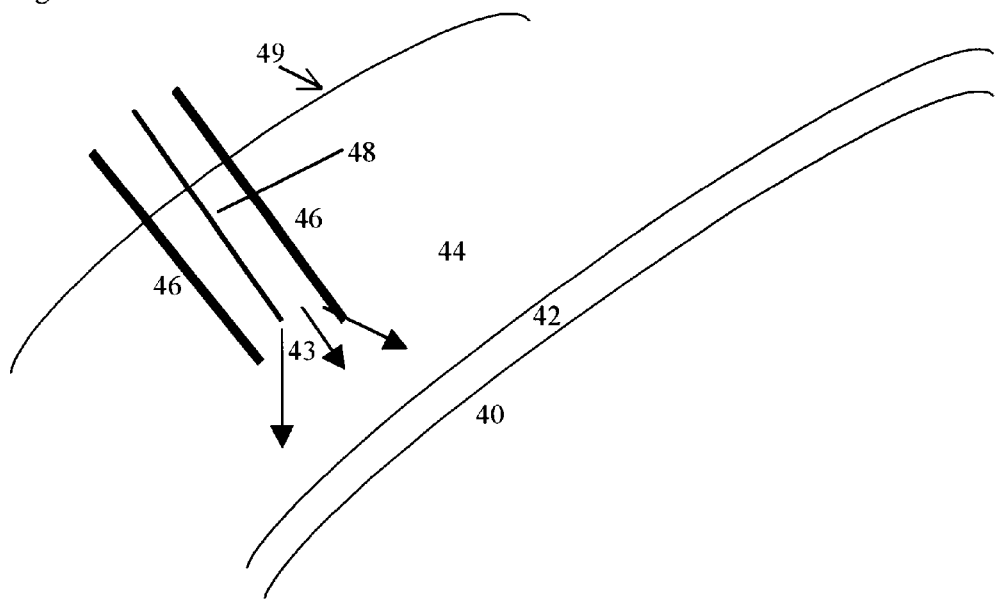
FIG. 4 depicts the use of a needle to place fiber close enough to irradiate a medical device within tissue as described in the present invention.

In most embodiments of the present invention either the medical device can be modified to apply radiation to the desired site, or the medical device surface can be irradiated through a shallow area of skin and tissue. It is possible however, that a highly specialized device prone to bacterial infection may not be readily adaptable to the incorporation of an optical fiber, and that the device may be too deeply situated to be irradiated through the skin without damage to the skin and underlying tissue. In this instance as before, the device is manufactured with the photosensitizing coating on or secreted from its appropriate surfaces. The photosensitizing coating is applied to the medical device surfaces where bacteria are likely to attach and grow. An optical fiber as depicted in FIG. 4 is then inserted using a needle through the tissue to get close enough to irradiate the medical device surfaces susceptible to bacterial attachment and growth.

Needle 46 is inserted through skin surface 49 and surrounding tissue 44 to be in proximity with medical device surface 40. The proximal end of optical fiber 48 is connected to a suitable medical laser. The distal end of optical fiber 48 is then inserted through needle 46. Coating 42 is then activated by irradiation 43 from fiber 48. While this method is certainly more invasive than the previous examples, it is still minimally invasive compared to the removal and replacement of the device due to bacterial encrustation and inflammation. This method is not directed to most medical procedures, but it is a good alternative when entry through an existing lumen isn't possible, no lumen exists or the device isn't shallow enough to be irradiated through the skin and tissue.

Having described preferred embodiments of the invention with reference to the accompanying drawings, it is to be understood that the invention is not limited to the precise embodiments, and that various changes and modifications may be effected therein by skilled in the art without departing from the scope or spirit of the invention as defined in the appended claims.

What is claimed is:

1. A bacteria resistant medical device comprising:
   surfaces having a photosensitizing compound in proximity to or in contact with said surfaces, to provide means to prevent attachment and growth of bacteria and microorganisms; and
   means to permit activation of said photosensitizing compound by irradiation with a suitable light source while portions of said device to be irradiated reside under a patient's skin.

2. A medical device according to claim 1, wherein said means to permit activation of said photosensitizing compound comprises a wall and said surfaces manufactured from material that is sufficiently translucent to a wavelength required for activating said photosensitizing compound and preferably is essentially transparent to said wavelength.

3. A medical device according to claim 1, wherein said means to permit activation of said photosensitizing compound comprises a wall containing at least two ports running longitudinally into which optical fibers may be placed and said wall and said surfaces being manufactured from material that is sufficiently translucent to a wavelength required for activating said photosensitizing compound and preferably is essentially transparent to said wavelength.

4. A medical device according to claim 1, wherein said photosensitizing compound upon activation produces singlet oxygen to destroy said bacteria and micro-organisms.

5. A medical device according to claim 1, wherein said photosensitizing compound is immobilized on said surface.

6. A medical device according to claim 1, wherein said photosensitizing compound is initially present in a dormant state.

7. A medical device according to claim 1, wherein said photosensitizing compound is releasable from said surface.

8. A medical device according to claim 1, wherein said photosensitizing compound is incorporated into a layer below said surface and is releasable through said surface.

9. A medical device according to claim 7 wherein said released photosensitizing compound then adheres onto or near said surface.

10. A medical device according to claim 8 wherein said released photosensitizing compound then adheres onto or near said surface.

11. A bacteria resistant medical device comprising:
- at least one surface, wherein said surface has means to retain a photosensitizing compound in proximity to said surface;
- means to introduce said photosensitizing compound to said surface from an outside source to fight bacterial growth and attachment on said surface while portions of said surface to be irradiated reside under a patient's skin;
- wherein said photosensitizing compound is chosen to aid in the destruction of selected microorganisms/bacteria, and wherein said photosensitizing compound is activatable by a suitable light source.

12. A medical device according to claim 11 wherein said photosensitizing compound is specifically chosen to produce singlet oxygen to destroy said microorganisms/bacteria.

13. A method to fight bacterial attack on medical devices comprising the steps of:
- applying a photosensitizing compound to at least some of a medical device's surfaces;
- introducing said medical device into a patient's body and beginning treatment;
- applying radiation, at some selected later time, to said surfaces with a suitable wavelength to activate said photosensitizing compound, while said device is still within said patient's body;
- generating singlet oxygen by said activated photosensitizing compound; and
- eliminating bacteria and preventing bacterial encrustation of said device.

14. A method according to claim 13, wherein said step of applying radiation is selectively repeated at periodic intervals.

15. A method according to claim 13, wherein said step of applying radiation is accomplished by irradiation through skin and tissue to reach said medical device.

16. A method according to claim 13, wherein said step of applying radiation is accomplished by transmitting said radiation through an optical fiber.

17. A method according to claim 16 further comprising the steps of:
- inserting said optical fiber toward a distal end of said medical device; and
- withdrawing said optical fiber at some predetermined rate to apply an appropriate dosage of light energy per square inch.

18. A method according to claim 17, wherein said step of inserting introduces said optical fiber into said medical device and said activation of said photosensitizing compound occurs by transmitting radiation through a wall between said optical fiber and said device's surfaces, said wall and surfaces being sufficiently translucent and preferably being essentially transparent to said suitable wavelength.

19. A method according to claim 18, wherein said insertion step is introducing said optical fiber through a port incorporated into said device.

20. A method according to claim 18, wherein said insertion step is inserting said optical fiber through an existing lumen in said medical device.

21. A method according to claim 16, wherein said optical fiber has a diffusing tip at its distal end, thus applying radiation to activate said photosensitizing compound in a geometrically broader manner.

22. A method according to claim 13, wherein said radiation step further comprises the steps of:
- irradiating said photosensitizing compound with a first wavelength to excite a dormant photo sensing compound into an active state; and
- irradiating said active state of said photosensitizing compound with a second wavelength to activate said photosensitizing compound.

* * * * *